(12) United States Patent
Ein-Gal

(10) Patent No.: US 11,642,543 B2
(45) Date of Patent: May 9, 2023

(54) COMBINED PULSED ELECTROMAGNETIC FIELD AND LOW INTENSITY SHOCKWAVE SYSTEM AND METHOD

(71) Applicant: Moshe Ein-Gal, Ramat Hasharon (IL)

(72) Inventor: Moshe Ein-Gal, Ramat Hasharon (IL)

( * ) Notice: Subject to any disclaimer, the term of this patent is extended or adjusted under 35 U.S.C. 154(b) by 0 days.

(21) Appl. No.: 17/892,303

(22) Filed: Aug. 22, 2022

(65) Prior Publication Data

US 2022/0409915 A1   Dec. 29, 2022

Related U.S. Application Data

(63) Continuation of application No. 17/016,714, filed on Sep. 10, 2020.

(51) Int. Cl.
*A61N 2/00* (2006.01)
*A61N 2/02* (2006.01)

(52) U.S. Cl.
CPC ............... *A61N 2/002* (2013.01); *A61N 2/02* (2013.01)

(58) Field of Classification Search
CPC . A61N 2/00; A61N 2/02; A61N 2/002; A61N 2/004
See application file for complete search history.

(56) References Cited

U.S. PATENT DOCUMENTS

| | | | | |
|---|---|---|---|---|
| 4,924,858 A * | 5/1990 | Katona | ..................... | G10K 9/12 |
| | | | | 367/175 |
| 2017/0087373 A1* | 3/2017 | Schwarz | ................. | A61N 2/004 |
| 2020/0390997 A1* | 12/2020 | Jovanov | ................. | A61H 23/02 |

* cited by examiner

*Primary Examiner* — Samuel G Gilbert
(74) *Attorney, Agent, or Firm* — Dekel Patent Ltd.; David Klein

(57) ABSTRACT

A method of treatment includes using an electrical energizing source coupled to a current conducting coil to cause the current conducting coil to produce pulsed electromagnetic fields. A conducting membrane is placed adjacent the current conducting coil and an insulating coupling interface is placed adjacent the membrane, such that the membrane is between the current conducting coil and the insulating coupling interface. One portion of the pulsed electromagnetic fields is intercepted by the membrane so that the membrane oscillates to generate acoustic waves to tissue adjacent the insulating coupling interface and another portion of the pulsed electromagnetic fields propagates through the insulating coupling interface to the tissue.

10 Claims, 1 Drawing Sheet

COMBINED PULSED ELECTROMAGNETIC FIELD AND LOW INTENSITY SHOCKWAVE SYSTEM AND METHOD

FIELD OF THE INVENTION

The present invention generally relates to a method and device for combining pulsed electromagnetic field therapy with low intensity shockwave treatment, such as for treating the area of the pelvis, peritoneum or penis, e.g., for treatment of erectile dysfunction or other tissues and parts of the body.

BACKGROUND OF THE INVENTION

Pulsed electromagnetic fields may be used for nerve or brain stimulation, treating ailments like joint and muscle pain, and assisting with the healing of broken bones and fractures.

A number of pulsed electromagnetic field therapy devices are available which produce pulsed electromagnetic fields to provide a physiological effect. They typically include a resonant circuit formed from a capacitor connected to a coil looped inductor through a switch (such as a semiconductor or spark gap switch). With the switch open, the capacitor can be pre-charged before closing the switch to discharge the capacitor into the inductor to initiate oscillation of the resonant circuit. The resonant circuit then oscillates until the energy stored in the resonant circuit is dissipated by the circuitry and the load. As the resonant circuit oscillates, it generates a sequence of electromagnetic oscillations in the coil looped inductor which is placed adjacent to, or around, a part of the body where the physiological effect of the pulsed electromagnetic field is desired.

Low intensity shockwaves (LISW) applied to soft tissue are known to increase blood flow in the tissue. LISW has been used to treat erectile dysfunction (ED), by increasing blood flow to the corpus cavernosum. Low intensity shockwaves are pulsed acoustic waves whose wave front is not necessarily steep as is characteristic of high intensity shockwaves.

SUMMARY OF THE INVENTION

The present invention seeks to provide a novel combination of pulsed electromagnetic field (PEMF) therapy with low intensity shockwave treatment (particularly electromagnetic low intensity shockwaves (ELIS)), such as for treating the area of the pelvis, peritoneum or penis, e.g., for treatment of erectile dysfunction (ED) or Peyronie's disease (also known as induratio penis plastica), or other tissues and parts of the body, as is described more in detail hereinbelow. In the case of ED, the invention can significantly improve penile hemodynamics required for erection.

In the invention, both PEMF and ELIS (or simply LIS) use current conducting coils to produce pulsed electromagnetic fields. The pulsed electromagnetic field is applied directly to the target organ or tissue while the LIS field induces current in an adjacent conductive membrane, causing the membrane to jerk and produce acoustic waves.

In one embodiment, a combined PEMF/LIS transducer includes a current conducting coil for producing a pulsed electromagnetic field, a thin conductive membrane, and a membrane-attached insulating coupling interface, generally transparent to acoustic waves. Current pulses delivered to the conducting coil produce an electromagnetic field. One portion of the electromagnetic field is intercepted by the membrane, giving rise to acoustic waves (low intensity shockwaves) propagated via the membrane-attached insulating coupling interface in the direction of the tissue (throughout, "tissue" encompasses either any tissue or any organ or both). Another portion of the electromagnetic field directly propagates in the direction of the tissue as a pulsed electromagnetic field. The geometry and dimensions of the coil and membrane determine the respective distributions of pulsed electromagnetic and acoustic fields in the tissue.

In another embodiment, there are separate coils for PEMF and LIS, and a timing controller controls and triggers the respective current pulses. Accordingly, the coil and membrane geometry may be selected or adjusted and the respective trigger timing may be controlled for respectively producing electromagnetic and acoustic fields at desired time intervals, e.g., for coinciding in time and space at desired tissue depth, due to different propagation speed of electromagnetic and acoustic waves.

There is provided in accordance with a non-limiting embodiment of the invention a method of treatment including using an electrical energizing source coupled to a current conducting coil to cause the current conducting coil to produce pulsed electromagnetic fields, wherein a membrane is placed adjacent the current conducting coil and an insulating coupling interface is placed adjacent the membrane, such that the membrane is between the current conducting coil and the insulating coupling interface, wherein one portion of the pulsed electromagnetic fields is intercepted by the membrane so that the membrane oscillates to generate acoustic waves to tissue adjacent the insulating coupling interface and another portion of the pulsed electromagnetic fields propagates to the tissue.

The insulating coupling interface may be made of an acoustically transparent material.

A controller may be coupled to the energizing source and/or to the current conducting coil to control a shape, a duration, an intensity or other parameter of the pulsed electromagnetic fields.

The method may include using geometry and dimensions of the current conducting coil and the membrane to determine respective distributions of pulsed electromagnetic and acoustic fields in the tissue.

The method may include using separate current conducting coils to generate pulsed electromagnetic fields and to generate acoustic waves.

The method may include using a controller to control operating parameters of pulses of the coils for generating the pulsed electromagnetic fields and the acoustic waves, and to control timing between pulses of the coils (e.g., at desired time intervals). The separate current conducting coils may be arranged in a pattern.

BRIEF DESCRIPTION OF THE DRAWINGS

The present invention will be understood and appreciated more fully from the following detailed description, taken in conjunction with the drawings in which.

DETAILED DESCRIPTION

Figure 1:
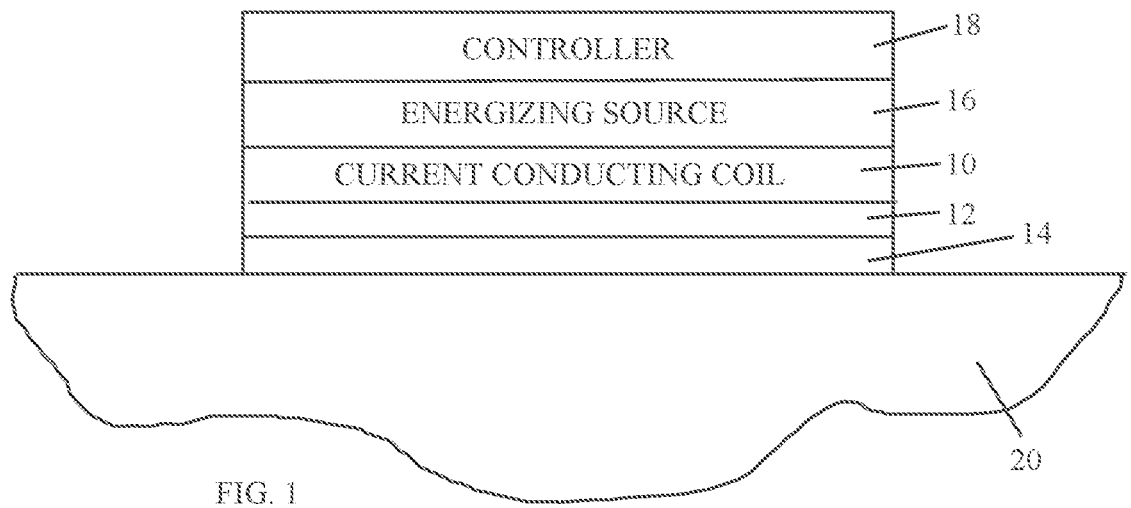
FIG. 1 is a simplified illustration of a combined pulsed electromagnetic field (PEMF) and low intensity shockwave (LIS) system, operative in accordance with a non-limiting embodiment of the present invention.

Reference is now made to FIG. 1, which illustrates a combined pulsed electromagnetic field (PEMF) and low intensity shockwave (LIS) system, operative in accordance with an embodiment of the present invention.

The system may include a current conducting coil 10 to produce pulsed electromagnetic fields. A thin (e.g., conductive) membrane 12 is placed adjacent (e.g., underneath) the current conducting coil 10. A membrane-attached insulating coupling interface 14 is placed adjacent (e.g., underneath) membrane 12, such that membrane 12 is between current conducting coil 10 and coupling interface 14.

The membrane-attached coupling interface 14 is made of an acoustically transparent material, such as a matrix or substrate of an acoustically transmissive material. In some embodiments, an acoustically transmissive material transmits at least about 70%, at least about 80%, at least about 90%, or at least about 95% of the acoustic wave energy from one surface to the another surface. In some embodiments, an acoustically transmissive material loses less than about 1 dB, less than about 2 dB, less than about 3 dB, less than about 4 dB, less than about 7 dB, or less than about 10 dB of sound energy from one side to the other side. A suitable acoustically transparent material is the material commercially available as a LITTMAN CARDIOLOGY III diaphragm (from 3M, Minneapolis, Minn., USA), which is used for stethoscopes. Some woven cotton or linen fabrics are also acoustically transparent.

An electrical energizing source 16 is coupled to current conducting coil 10 to produce the pulsed electromagnetic fields. A controller 18 may be coupled to electrical energy source 16 and/or coil 10 to control the shape, duration and other parameters of the pulsed electromagnetic fields.

Current pulses delivered to conducting coil 10 produce an electromagnetic field. One portion of the electromagnetic field is intercepted by membrane 12 so that induced current in membrane 12 causes membrane 12 to move rapidly, which generates acoustic waves (low intensity shockwaves) delivered via coupling interface 14 to a tissue 20 (throughout, "tissue" encompasses either any tissue or any organ or both). Another portion of the electromagnetic field propagates away from membrane 12 directly or through the coupling interface 14 to the tissue 20 as a pulsed electromagnetic field. The geometry and dimensions of the coil and membrane determine the respective distributions of pulsed electromagnetic and acoustic fields in the tissue.

Low intensity shockwaves and pulsed electromagnetic waves may use different interfaces. LIS requires insulating, acoustically transparent, membrane attached, coupling interface; EM waves require insulating, EM-transparent, off-membrane interface of material like silicone, plastic or air. Using the same interface material for both LIS and EM waves is possible but not necessary.

Figure 2:
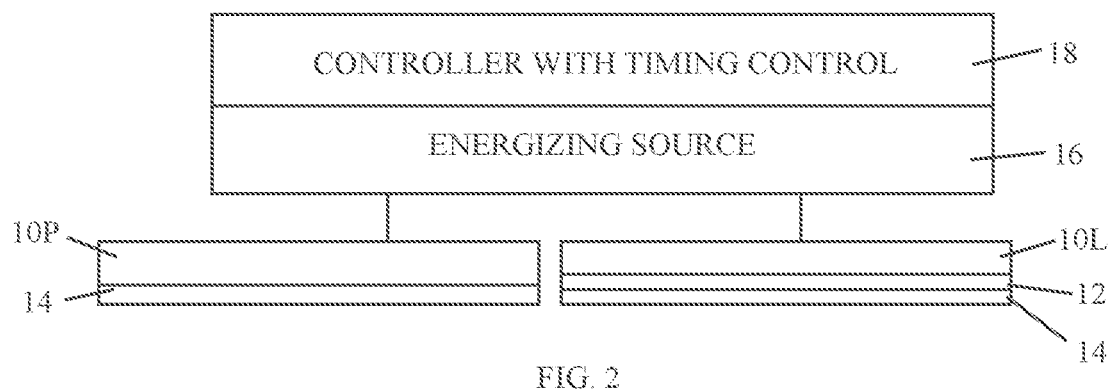
FIG. 2 is a simplified illustration of a combined PEMF and LIS system with time control, operative in accordance with another non-limiting embodiment of the present invention.

Reference is now made to FIG. 2. In this embodiment, there are separate coils 10P and 10L for PEMF and LIS. The controller 18 is a timing controller that controls and triggers the respective current pulses.

Figure 3:
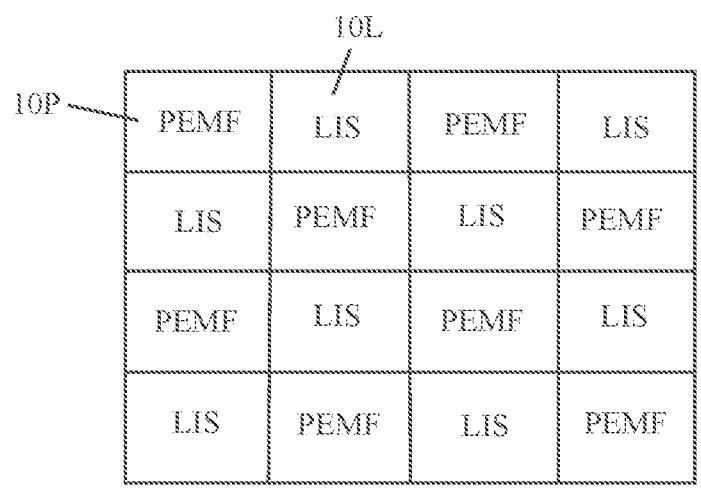
FIG. 3 is a simplified illustration of a combined PEMF and LIS system with time and spatial control, operative in accordance with another non-limiting embodiment of the present invention.

Reference is now made to FIG. 3, which is similar to FIG. 2 in that there are separate PEMF and LIS coils, except that in FIG. 3 these different coils are arranged in a pattern, such as alternating segments in a matrix. Accordingly, in the embodiments of FIGS. 2 and 3, the coil and membrane geometry may be selected or adjusted and the respective trigger timing may be controlled for producing electromagnetic and acoustic fields at desired time intervals, e.g., for coinciding in time and space.

What is claimed is:

1. A method of treatment comprising:
using an electrical energizing source coupled to a current conducting coil to cause said current conducting coil to produce pulsed electromagnetic fields, wherein a conducting membrane is placed adjacent said current conducting coil and an insulating coupling interface is placed adjacent said membrane, such that said membrane is between said current conducting coil and said insulating coupling interface;
wherein one portion of said pulsed electromagnetic fields is intercepted by said membrane so that induced current in said membrane causes the membrane to move rapidly and generate acoustic waves to tissue adjacent said insulating coupling interface and another portion of said pulsed electromagnetic fields propagates away from the membrane through said coupling interface to said tissue.

2. The method according to claim 1, wherein said insulating coupling interface is made of an acoustically transparent material.

3. The method according to claim 1, comprising using a controller coupled to said energizing source and/or to said current conducting coil to control a shape, a duration, an intensity or other parameter of said pulsed electromagnetic fields.

4. The method according to claim 1, comprising using geometry and dimensions of said current conducting coil and said membrane to determine respective distributions of pulsed electromagnetic and acoustic fields in said tissue.

5. The method according to claim 1, comprising using separate current conducting coils to respectively generate pulsed electromagnetic fields and to generate acoustic waves.

6. The method according to claim 5, comprising using a controller to control operating parameters of pulses of said coils for generating said pulsed electromagnetic fields and said acoustic waves, and to control timing between pulses of said coils.

7. The method according to claim 5, wherein said separate current conducting coils are arranged in a pattern.

8. The method according to claim 1, comprising using a combination of said pulsed electromagnetic fields and said acoustic waves to treat organs or tissue in a pelvis, legs, a back or a shoulder.

9. The method according to claim 1, comprising using a combination of said pulsed electromagnetic fields and said acoustic waves to treat erectile dysfunction (ED) or pain in different body regions.

10. Apparatus for treatment comprising:
an electrical energizing source coupled to a current conducting coil to cause said current conducting coil to produce pulsed electromagnetic fields, wherein a membrane is placed adjacent said current conducting coil and an insulating coupling interface is placed adjacent said membrane, such that said membrane is between said current conducting coil and said insulating coupling interface;
wherein one portion of said pulsed electromagnetic fields generated by said current conducting coil is intercepted by said membrane so that induced current in said membrane causes the membrane to rapidly move and generate acoustic waves to tissue adjacent said insulating coupling interface and another portion of said pulsed electromagnetic fields propagates away from the membrane through said coupling interface to said tissue.

\* \* \* \* \*